US005585251A

United States Patent [19]
Alder et al.

[11] Patent Number: 5,585,251
[45] Date of Patent: Dec. 17, 1996

[54] FUNGAL ISOLATES, FUSACANDINS

[75] Inventors: Lisa A. Alder, Lindenhurst; Neal S. Burres, Libertyville; Jill E. Hochlowski, Green Oaks; Marianna Jackson, Waukegan; James B. McAlpine, Libertyville, all of Ill.

[73] Assignee: Abbott Laboratories, Abbott Park, Ill.

[21] Appl. No.: 370,934

[22] Filed: Jan. 10, 1995

[51] Int. Cl.$^6$ .......................... C12P 19/44; A61K 31/70; C07H 15/00
[52] U.S. Cl. ................... 435/75; 435/74; 514/25; 536/16.8
[58] Field of Search ................... 514/25; 435/74, 435/75; 536/16.3

[56] References Cited

U.S. PATENT DOCUMENTS

| | | | |
|---|---|---|---|
| 4,278,665 | 7/1981 | Traxler et al. | 536/16.8 |
| 5,008,187 | 4/1991 | Chaiet et al. | 435/72 |

*Primary Examiner*—Elli Peselev
*Attorney, Agent, or Firm*—Mona Anand; Thomas D. Brainard

[57] ABSTRACT

Novel antifungal agents having the formula:

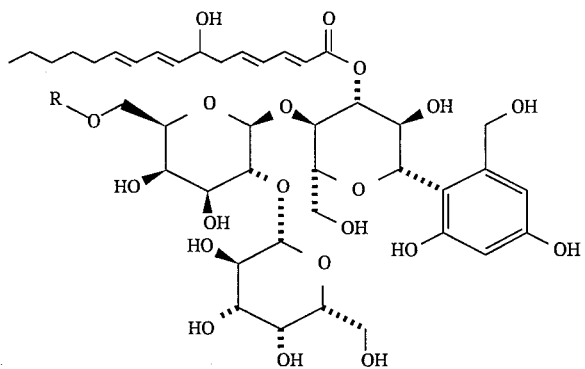

wherein R is hydrogen or a radical of the formula

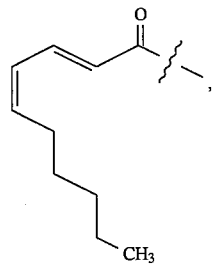

and pharmaceutically acceptable prodrugs thereof, as well as (i) pharmaceutical compositions comprising such compounds, (ii) methods of treatment using such compounds, and (iv) methods and fungal cultures useful in making the same.

11 Claims, 6 Drawing Sheets

FUNGAL ISOLATES, FUSACANDINS

TECHNICAL FIELD

The present invention relates to novel fungal isolates of potential medicinal value. More particularly, the invention relates to compounds isolated from cultures of the Fusarium genus, herein designated "fusacandins", which possesses antifungal activity, as well as to methods and cultures of microorganisms useful for the preparation of fusacandins, pharmaceutical compositions containing such compounds, and the use thereof in treating fungal infections.

BACKGROUND OF THE INVENTION

The compounds of the present invention are related to those of the papulacandin class, described in *J. Antibiotics* 33(9):967–977 (1980). Papulacandins include BE-29602, disclosed in a published Japanese patent application of Banyu Pharmaceutical Co. (No. JP05170784-A, published Jul. 9, 1993) and isolated from a Fusarium species of fungus, and chaetiacandin, disclosed in *J. Antibiotics* 38(4):455–459 (1985) and *J. Antibiotics* 38(4):544–546 (1985). The fusacandins are distinct from the papulacandin compounds, however, in that they contain three sugar moieties not previously described in connection with other members of this class.

SUMMARY OF THE INVENTION

It has now been found that novel antifungal agents of the papulacandin class, herein designated "fusacandins", may be obtained by the fermentation of certain cultures belonging to the fungal strain Fusarium sp. AB 1900A-1314.

Accordingly, in one aspect of the present invention are disclosed compounds of the formula:

as well as pharmaceutically acceptable prodrugs thereof.

In the above formula (I), R may be a radical of the formula in which instance the compound is designated fusacandin A. Alternatively, the radical R may be hydrogen, in which instance the compound is designated fusacandin B.

In another aspect of the present invention are disclosed pharmaceutical compositions which comprise a compound of the invention in combination with a pharmaceutically acceptable carrier.

In a further aspect of the invention is disclosed a method of suppressing or inhibiting a fungal infection in a patient in need of such treatment, comprising administering to the patient a therapeutically effective amount of a compound of the invention.

In yet another aspect of the invention, a process for preparing the compounds of the invention is disclosed which comprises the steps of (a) culturing a microorganism having substantially all the characteristics of Fusarium species AB 1900A-1314 under suitable conditions in a fermentation medium containing assimilable sources of carbon and nitrogen; (b) allowing the desired compound to accumulate in the fermentation medium; and (c) isolating the compound from the fermentation medium. Preferably, the microorganism to be cultured is Fusarium strain NRRL 21252 or a mutant or derivative thereof.

Similarly, in an additional aspect of the present invention is disclosed a biologically pure culture of a microorganism capable of producing the compounds of the invention, namely, a microorganism having substantially all the characteristics of Fusarium species AB 1900A-1314. Preferably, the microorganism is Fusarium strain NRRL 21252 or a mutant or derivative thereof.

BRIEF DESCRIPTION OF THE DRAWINGS

The present invention will be better understood in connection with the following figures, in which.

DETAILED DESCRIPTION OF THE INVENTION

As used throughout this specification and in the appended claims, the following terms have the meanings specified:

The term "biologically pure" as used herein refers to fungal cultures which are substantially free from biologically active contaminants.

The term "mutant or derivative" as used herein refers to fungal strains which are obtained by mutagenization or genetic modification of Fusarium species strain NRRL 21252 by techniques readily known in the art.

The term "pharmaceutically acceptable prodrug" as used herein refers to those prodrugs of the compounds of the present invention which are, within the scope of sound medical judgement, suitable for use in contact with the tissues of humans and lower animals without undue toxicity, irritation, allergic response, and the like, commensurate With a reasonable benefit/risk ratio, and which are effective for their intended use.

The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems,* Vol. 14 of the A.C.S. Symposium Series, and in Edward B. Roche, ed., *Bioreversible Carders in Drug Design,* American Pharmaceutical Association and Pergamon Press (1987). (Both here and throughout the specification, it is intended that citations to the literature are expressly incorporated by reference.)

Where appropriate, prodrugs of derivatives of compounds of the present invention may be prepared by any suitable method. For those compounds in which the prodrug moiety is an amino acid or peptide functionality, the condensation of the amino group with amino acids and peptides may be effected in accordance with conventional condensation methods such as the azide method, the mixed acid anhydride method, the DCC (dicyclohexyl-carbodiimide) method, the active ester method (p-nitrophenyl ester method, N-hydroxy-succinic acid imide ester method, cyanomethyl ester method and the like), the Woodward reagent K method, the DCC-HOBT (1-hydroxy-benzotriazole) method and the like. Classical methods for amino acid condensation reactions are described in M. Bodansky, Y. S. Klausner and M. A. Ondetti, *Peptide Synthesis,* Second Edition (New York, 1976).

Asymmetric centers may exist in the compounds of the present invention. Except where otherwise noted, the present invention contemplates the various stereoisomers and mixtures thereof.

The compounds of the invention exhibit in vitro activity as antifungal agents against a variety of fungal organisms and inhibit (1,3)-β-glucan synthetase. They are therefore expected to be useful in the treatment of fungal infections in mammals. When used in such treatment, a therapeutically effective amount of the compound of the present invention may be employed in pure form or, where such forms exist, in pharmaceutically acceptable salt, ester or prodrug form. Alternatively, the compound may be administered as pharmaceutical compositions containing the compound of interest in combination with one or more pharmaceutically acceptable excipients. By a "therapeutically effective amount" of the compound of the invention is meant a sufficient amount of the compound to treat the targeted disorder, at a reasonable benefit/risk ratio applicable to any medical treatment, which is administered in such quantities and such a period of time as is necessary to obtain the desired therapeutic effect. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compound of this invention administered to a human or lower animal may range from about 0.1 to about 100 mg/kg/day. For purposes of oral administration, doses may be in the range of from about 1 to about 100 mg/kg/day or, more preferably, of from about 10 to about 20 mg/kg/day. If desired, the effective daily dose may be divided into multiple doses for purposes of administration; consequently, single dose compositions may contain such amounts or submultiples thereof as make up the daily dose.

The pharmaceutical compositions of the present invention comprise a compound of the invention and a pharmaceutically acceptable carrier or excipient, which may be administered orally, rectally, parenterally, intracisternally, intravaginally, intraperitoneally, topically (as by powders, ointments, or drops), bucally, or as an oral or nasal spray. By "pharmaceutically acceptable carrier" is meant a non-toxic solid, semi-solid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Pharmaceutical compositions of this invention for parenteral injection include pharmaceutically acceptable sterile nonaqueous solutions or aqueous dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be deskable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly-(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose and acacia, c) humectants such as glycerol, d) disintegrating agents such as agar-agar, calcium carbonate, potato or tapioca starch, alginic acid, certain silicates and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols and sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, olive, castor and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, and sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carders include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquified gas propellant. The liquified propellant medium and indeed the total composition is preferably such that the active ingredient does not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

The compound of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y., 1976, p. 33 et seq.

The compounds of the present invention may be produced by culturing, in appropriate media, fungal microorganisms which are capable of producing fusacandins. The compounds are produced when the culture is grown in a stationary fermentation with a culture medium containing a source of carbon and a source of nitrogen. Media which are useful include an assimilable source of carbon such as starch, sugar, molasses, glycerol, a combination of glucose plus molasses, etc.; an assimilable source of nitrogen such as protein, protein hydrolysate, polypeptides, amino acids, peptone plus yeast extract or whole yeast, etc.; and other optional organic and inorganic ingredients which can be added to stimulate production of the fusacandin compounds. For example, inorganic anions and cations including potassium, magnesium, calcium, ammonium, sulfate, carbonate, phosphate, chloride, etc. may be added to the medium. Further, buffers such as calcium carbonate can be added to aid in controlling the pH of the fermentation medium. The stationary fermentation may include a solid support to increase the surface area available for fungal growth. Suitable supports include Spoon Size Shredded Wheat, rolled oats, barley, cracked corn, flee, millet, corn bran, wheat bran, oat bran, vermiculite, etc. The culture may be incubated in stationary vessel (without movement) or in a cylindrical or other vessel which is rolled or agitated to increase aeration. Other culture methods, such as a liquid, submerged, agitated culture process are feasible. In these cases, aeration may be provided by forcing sterile air through the fermentation medium. Agitation can be provided by shaking the container or by stirring the culture, for example, with a mechanical stirrer. The fermentation is generally carried out in a temperature range of from about 15° C. to about 35° C. The pH of the fermentation is preferably maintained between 3 and 9. The compound is produced and accumulated between 3 and 28 days after inoculation of the fermentation medium.

Subsequent to the fermentation process, the fusacandin compounds can be extracted from the fermentation broth as for example with ethyl acetate/acetone solvent mixtures. Partial purification of the active components can be achieved by sequential trituration of the organic extract with organic solvents such as ethyl acetate, ethanol and methanol in order to selectively remove the desired organic compounds. The extracts may be further purified by use of various partitioning solvent systems such as, for example, chloroform/methanol/water, hexane/ethyl acetate/methanol/water, or ethanol/ethyl acetate/water. Further purification and separation of individual components can be achieved by counter-current chromatography in solvent systems such as, for example, ethyl acetate/ethanol/water, chloroform/methanol/water, or chloroform/carbon tetrachloride/methanol/water, and/or by adsorption onto silica gel and subsequent elution with organic solvents and solvent mixtures such as ethyl acetate, chloroform and methanol. Size exclusion chromatography on resin such as SEPHADEX LH-20, developed in a solvent such as methanol, affords the pure compound.

The compounds, processes and uses of the present invention will be better understood in connection with the following examples, which are intended as an illustration of and not a limitation upon the scope of the invention. The following abbreviations were used: EtOAc for ethyl acetate, EtOH for ethanol, MeOH for methanol and TLC for thin layer chromatography.

EXAMPLE 1

Identification and Characterization of of the Fusacandin-Producing Strain Fusarium Sp. Strain AB 1900A-1314

The compounds of the present invention, "fusacandins", were first obtained from a fungus isolated from a conk (fruiting body of wood-attacking fungus) collected in Piatt County, Illinois. The culture, which was designated strain AB 1900A-1314, is a Fusarium species as indicated by the production of characteristic macroconidia. A subculture of this microorganism was deposited in the permanent collection of the National Center for Agricultural Utilization Research, United States Department of Agriculture, 1815 North University Street, Peoria, Ill. 61604, U.S.A., under the terms of the Budapest Treaty, and accorded accession number NRRL 21252.

Strain AB 1900A-1314 was examined at the Pennsylvania State University, Fusarium Research Center, and identified as a strain of Fusarium sambucinum. The morphological and cultural characteristics of this strain grown on two media at 25° C. for seven days were as described below. The colors and numbers shown in parenthesis were assigned based on the Inter-Society Color Council-National Bureau of Standards (ISCC-NBS) Centroid Color Charts, U.S. Dept. of Commerce supplement to NBS Cir. 553, Washington D.C., 1976.

Colonies of strain AB 1900A-1314 on Potato Dextrose agar (Difco) were dense, floccose, medium yellow-pink (29), grew rapidly to 75–80 mm in diameter and produced a clear exudate. Aerial mycelium was pale pink in color (7) and the reverse was light orange (52) to medium orange (53). Spore structures were not found on this medium at seven days. As the culture aged, many raised, round, light orange (52) structures, 1–3 mm in diameter, developed on the agar surface. These aggregates were hard but could be broken apart by moderate pressure with an inoculating loop. Fragments of the structures under light microscopy consisted of flattened, irregular cells mixed with a few strands of mycelia. The aggregates appear to be similar to the perithecia-bearing stromata which *Fusarium sambucinum* (*Gibberella pulicaris*) can form on woody host tissue (Booth, C.: The Genus Fusarium. pp. 168–172, Commonwealth Mycological Institute, Kew, Surrey, England, 1971). Perithecia or asci, however, were not observed.

Colonies grew rapidly on Cornmeal agar (Difco) and attained a diameter of 75–80 mm in seven days. The culture produced characteristic four to six septate, sickle-shaped macroconidia and one to two septate microconidia on this medium. The colonies had white (263), wispy aerial mycelia and the reverse was colorless. Macroconidia were produced abundantly, measuring 37.5–70×5–7 μm while microconidia measured 20–37.5×3.75–7.5 μm. The culture developed medium orange (53) sporodochia after 14 days incubation on Cornmeal agar.

EXAMPLE 2

Growth of Fusarium Sp. Strain AB 1900A-1314 in Stationary Culture

The fusacandin-producing culture, Fusarium sp. AB 1900A-1314, was maintained as a frozen inoculum stock by freezing a portion of the original inoculum and storing at −70° C. The medium S18 (Table 1) was used for seed growth and the medium F9 (Table 2) was used for stationary fermentations.

TABLE 1

Seed Medium S18

| Ingredients | grams/liter |
| --- | --- |
| Corn steep powder (Roquette Corp., Gurnee, IL) | 2.5 |
| Glucose monohydrate | 10.0 |
| Oat flour (National Oats Co., Cedar Rapids, IA) | 10.0 |
| Tomato paste (made by Contadina Foods, Inc. Los Angeles, CA) | 40.0 |
| $CaCl_2.2H_2O$ | 10.0 |
| Trace element solution | 10 mL/L |

Distilled water was added to achieve a volume of 1 liter. The pH was adjusted to pH 6.8. Reference: Goetz et al., *J. of Antibiotics* 38: 1633–1637 (1985).

Trace Element Solution

| Ingredients | grams/liter |
| --- | --- |
| $FeSO_4.7H_2O$ | 1.0 |
| $MnCl_2.4H_2O$ | 1.0 |
| $CuCl_2.2H_2O$ | 0.025 |
| $CaCl_2.2H_2O$ | 0.1 |
| $H_3BO_3$ | 0.56 |
| $(NH_4)_6MoO_2.4H_2O$ | 0.019 |
| $ZnSO_4.7H_2O$ | 0.2 |

Distilled water was added to achieve a volume of 1 liter.

TABLE 2

Fermentation Medium F9

| Ingredients | grams/liter |
| --- | --- |
| Lactose | 24.0 |
| Peptone (made by Difco Laboratories, Detroit, MI) | 16.0 |
| $MgSO_4.7H_2O$ | 0.4 |
| $KH_2PO_4$ | 2.08 |
| $NaNO_3$ | 1.28 |
| $ZnSO_4.7H_2O$ | 0.004 |

Distilled water was added to achieve a volume of 1 liter without pH adjustment. Spoon Size Shredded Wheat (Nabisco Brands, Inc., East Hanover, N.J.) was used as solid growth support, following separate sterilization.

The seed flasks were prepared by dispensing 100 mL of the seed medium (Table 1 ) into 500 mL Erlenmeyer flasks. The flasks were sterilized for 30 minutes at 121° C., 15 psi. Inoculum for the fermentation was prepared by inoculating 1% of the frozen inoculum into each of several seed flasks. The seed flasks were incubated for 72 hours at 28° C. C on a rotary shaker, operated at 225 rpm, with a stroke of 2 inches (approximately 5 cm).

The fermentation was conducted in 3 glass 20-liter carboys. Each carboy, containing 300 grams of Spoon Size Shredded Wheat, was sterilized for 45 minutes at 121° C., 15 psi. The F9 fermentation medium was sterilized in 3 batches of 360 mL in 2-liter Erlenmeyer flasks. Sterilization was at 121° C., 15 psi.

The 360 mL of liquid medium was inoculated with 60 mL of 72 hour seed growth. The combination was mixed and added aseptically to a carboy containing 300 grams of Shredded Wheat. The mixture was again thoroughly mixed to distribute the inoculum. The carboys were incubated in an upright position at 20° C. for 21 days. Three carboys were prepared in this manner.

EXAMPLE 3

Growth of Fusarium Sp. Strain AB 1900A- 1314 in Submerged Culture

The seed flasks were prepared by dispensing 600 mL of the seed medium (Table 3) into 2-liter Erlenmeyer flasks. The flasks were sterilized for 30 minutes at 121° C., 15 psi. Inoculum for the fermentation was prepared by inoculating 1% of the frozen inoculum into each of 3 seed flasks. The seed flasks were incubated for 72 hours at 28° C. on a rotary shaker, operated at 225 rpm, with a stroke of 2 inches (approximately 5 cm).

Thirty liters of production medium (Table 4) were prepared in a 42-liter, stainless steel, stirred fermentor (LH Fermentation) and sterilized at 121° C. and 15 psi for 1 hour. The antifoam agent XFO-371 (Ivanhoe Chemical Co,. Mundelein, Ill.) was added initially at 0.01%, and then as needed. The fermentor was inoculated with 1500 mL of the seed flask growth. The temperature was controlled at 28° C. The agitation rate was 250 rpm and aeration was 1.5 vol/vol/min. The head pressure was maintained at 5 psi. The fermentation was terminated at seven days, with a harvest volume of about 13 liters.

TABLE 3

Seed medium for submerged fermentation

| Ingredient | grams/liter |
| --- | --- |
| Mannitol | 20.0 |
| Soy flour | 20.0 |
| Distilled water | 1 liter |

Reference: Traxler et at., *J. Antibiotics* 30:289–296 (1977).

TABLE 4

Submerged fermentation medium

| Ingredient | grams/liter |
| --- | --- |
| Glucose monohydrate | 55.0 |
| Mannitol | 10.0 |
| Glycine | 2.0 |
| Dried lard water (Inland Molasses, Dubuque, IA) | 5.0 |
| Soybean meal (Archer Daniels Midland Co., Decatur, IL) | 5.0 |
| Sodium citrate | 2.0 |
| $KH_2PO_4$ | 2.0 |
| $CoCl_2.6H_2O$ | 0.01 |

Distilled water was added to achieve a volume of 1 liter without pH adjustment. Reference: VanMiddlesworth et al., *J. Antibiotics* 44:45–51 (1991).

EXAMPLE 4

Isolation of Fusacandin A from Stationary Culture

To 3 carboys containing stationary culture were added 3 liters of acetone. The resulting mixture was allowed to soak for 18 hours. This acetone extract was removed and an additional 6 liters of acetone added to the stationary culture, left to soak for 1 hour and removed. This procedure was repeated two additional times. The combined acetone extracts were concentrated to afford 29.7 grams of brown oil. This oil was triturated sequentially with 2 liters each of hexane, EtOAc, EtOH, MeOH and distilled water. The ethanol soluble material was concentrated to afford 400 mg of tan oil which was subjected to silica gel chromatography on 200 grams of VARIAN 40 μ silica gel eluted sequentially with 500 mL each of EtOAc, 5% MeOH in EtOAc, 10% MeOH in EtOAc, 25% MeOH in EtOAc, 50% MeOH in EtOAc, and 100% MeOH. The material which eluted with 10% MeOH in EtOAc was concentrated to afford 130 mg of a pale oil which was subjected to countercurrent chromatography on an Ito multi-layered coil planet centrifuge in a solvent system of $CHCl_3/MeOH/H_2O$ (1:1:1), lower layer stationary. Fractions of 5mL each were collected from this countercurrent chromatography with a solvent front at fraction 19, and fractions 43–45 were combined to yield 3.0 mg of a clear oil. This oil was subjected to size exclusion chromatography on a SEPHADEX LH-20 resin column developed in MeOH. The active fractions from this column were combined and concentrated to yield 1.8 mg of pure fusacandin A.

EXAMPLE 5

Isolation of Fusacandin A from Submerged Fermentation 15 liters of whole culture broth were added to 8 liters of acetone and the mixture was agitated for 1 hour, after which 15 liters of EtOAc was added, the mixture was agitated and the upper layer was removed. An additional two 8-liter extractions were made, combined with the first and concentrated under reduced pressure to yield 15 grams of brown oil. This oil was triturated sequentially with 2 liters each of hexane, EtOAc and MeOH. The MeOH soluble material was concentrated in vacuo to yield 780 mg of brown oil which was subjected to silica gel chromatography on 500 grams of VARIAN 40 μ silica gel eluting sequentially with 1 liter each of EtOAc, 2% MeOH in EtOAc, 5% MeOH in EtOAc, 10% MeOH in EtOAc, 20% MeOH in EtOAc, 50% MeOH in EtOAc and 100% MeOH. The material which eluted with 50% MeOH in EtOAc was subjected to size exclusion chromatography on a SEPHADEX LH-20 resin column developed in MeOH. Active fractions from this column were combined to yield 160 mg of pure fusacandin A.

EXAMPLE 6

Isolation of Fusacandin B from Submerged Fermentation

To 4900 liters of whole broth were added 3350 liters of acetone and 3700 liters of ethyl acetate. The resulting mixture was agitated for approximately 12 hours after which time the upper layer was removed, concentrated under reduced pressure, and deposited onto 10 kg of silica gel. This was loaded onto the top of a 240 kg silica gel column developed sequentially with 300 liters of EtOAc 300 liters of 25% MeOH in EtOAc, 300 liter of 50% MeOH in EtOAc, 300 liters of 75% MeOH in EtOAc and finally 300 liters of MeOH. A portion (25 g) of the material which eluted with 25% MeOH in EtOAc was partitioned between 3:1:2 EtOAc/EtOH/$H_2O$, and the upper layer from this partition was concentrated under reduced pressure to an oily solid residue. This residue was subjected to size exclusion chromatography on a SEPHADEX LH-20 resin column developed in MeOH. The active fractions from this column were combined based upon their behavior on thin layer chromatograph to yield fusacandin A (2.65 g) and fusacandin B (62 mg).

EXAMPLE 7

Physico-Chemical Characterization of the Fusacandins

Figure 1:
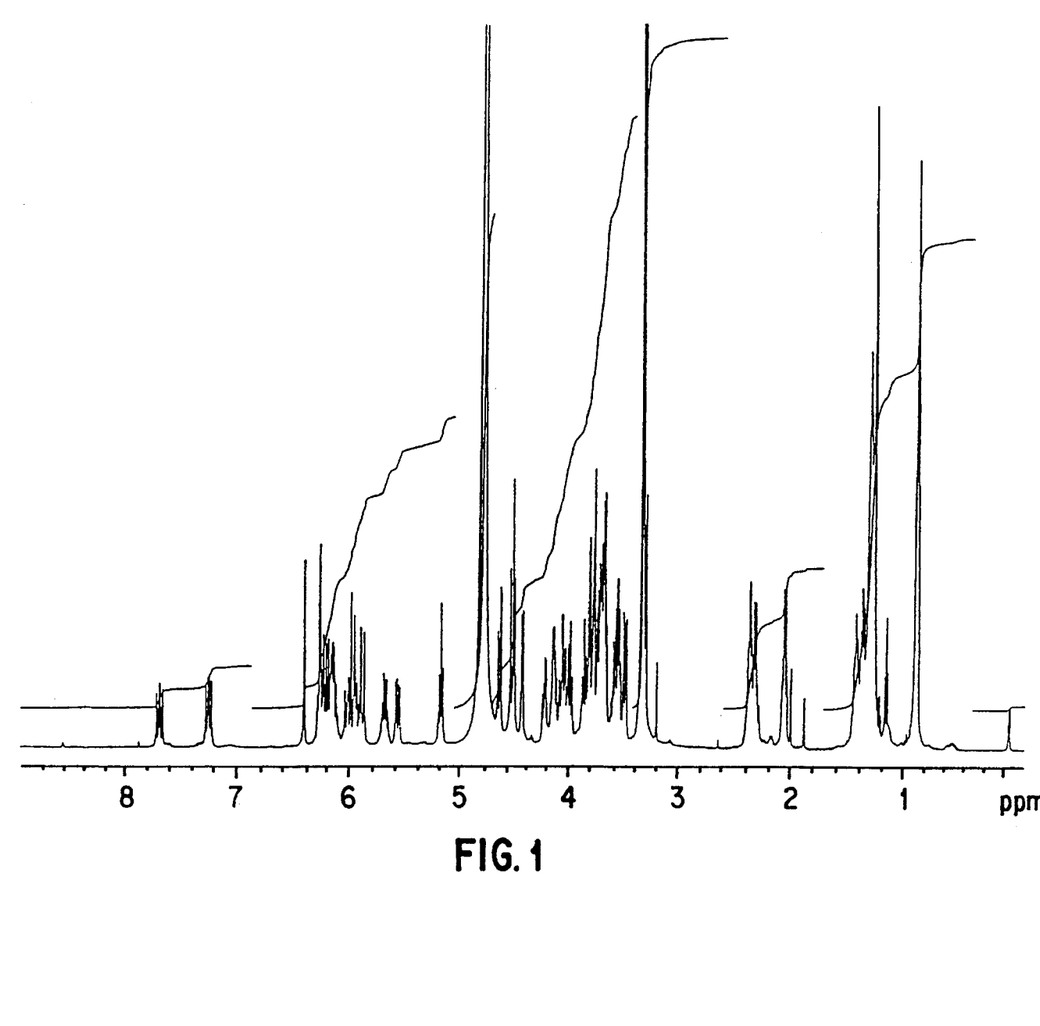
FIG. 1 is a proton nuclear magnetic resonance (NMR) spectrum of Fusacandin A in $CD_3OD$.
Figure 2:
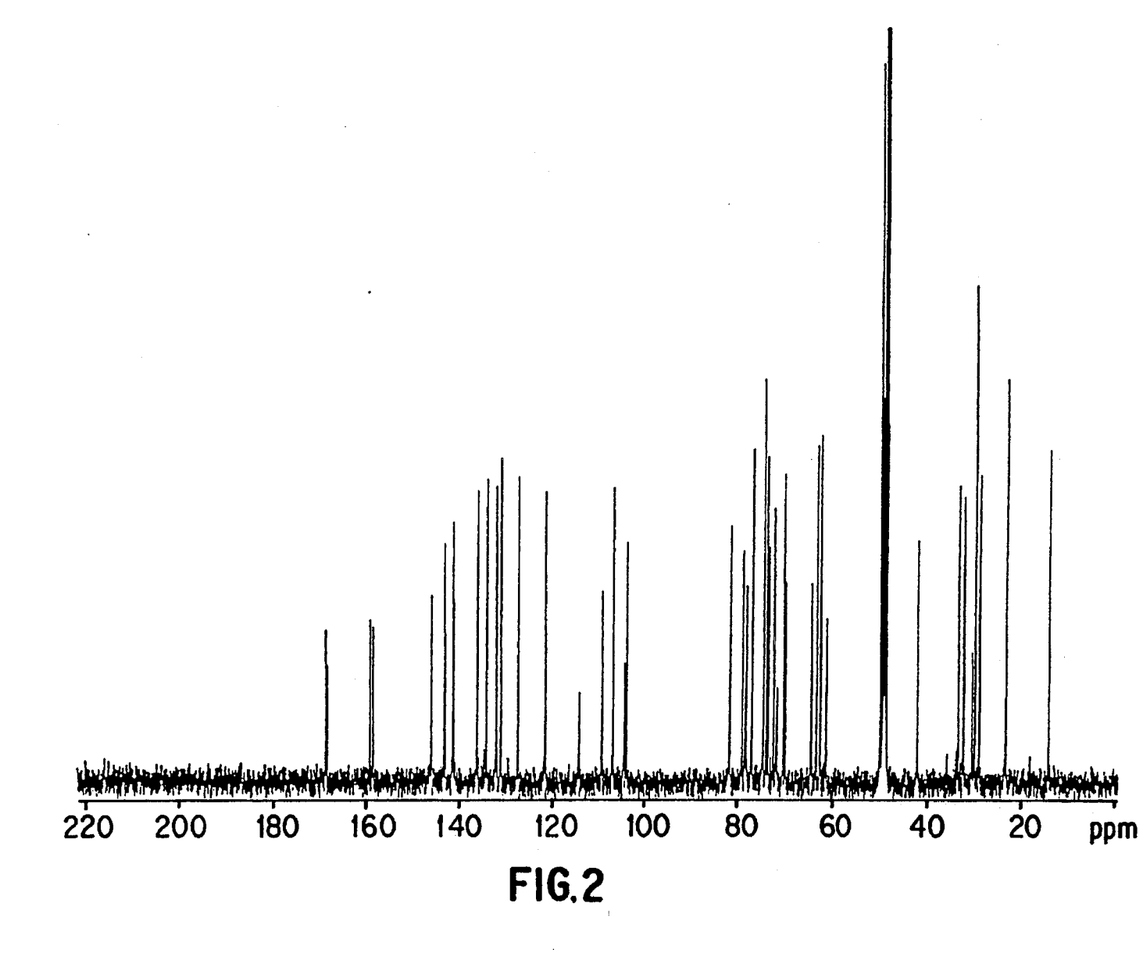
FIG. 2 is a carbon NMR spectrum of Fusacandin A in $CD_3OD$.
Figure 3:
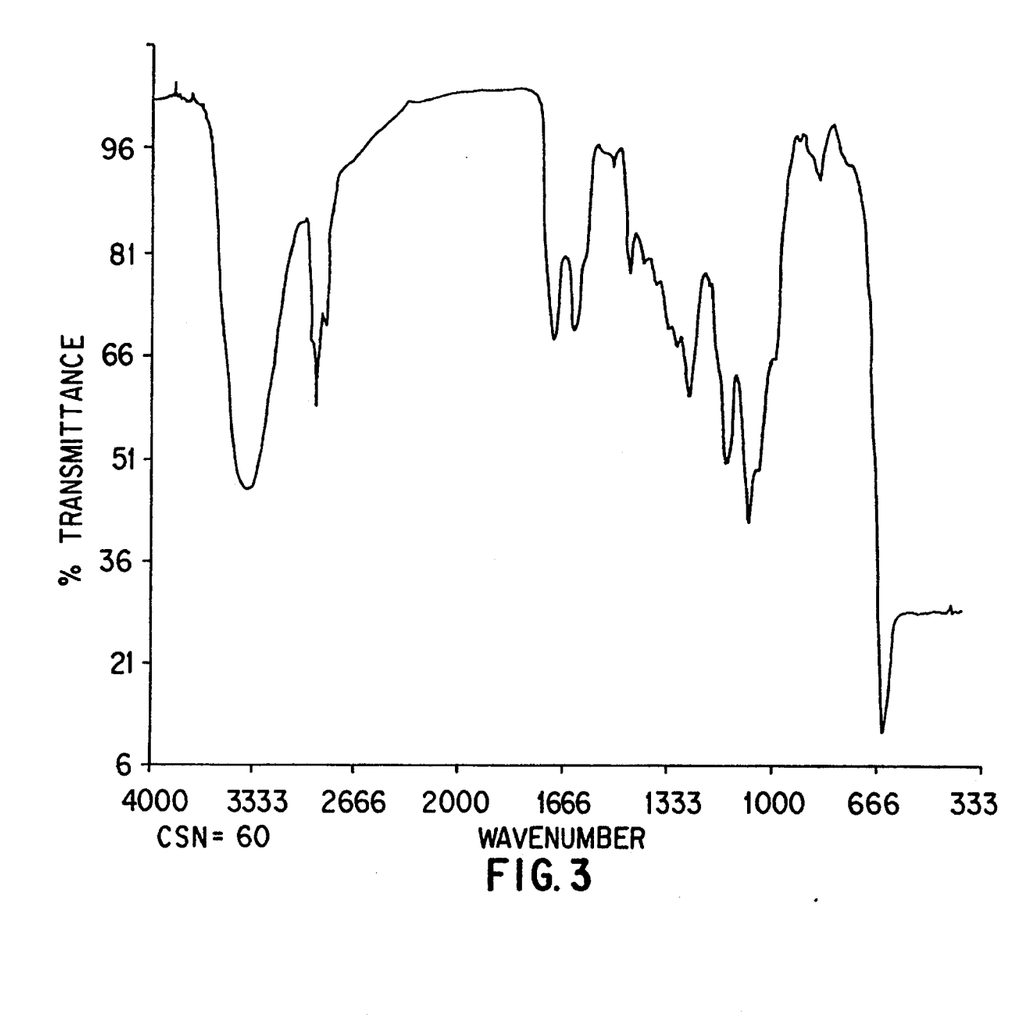
FIG. 3 is an infrared (IR) spectrum of Fusacandin A acquired in microscope mode.

Fusacandin A was characterized using IR, UV, $^1H$ and $^{13}C$ NMR spectroscopy. The resulting infrared, proton and carbon spectra are shown in FIGS. 1, 2 and 3. Fusacandin A has a molecular weight of 1020 ($C_{51}H_{71}O_{21}$) and is a clear oil. $[\alpha]_D=+58°$ (c=0.67, MeOH). TLC characterization on Merck silica gel plates: Rf=0.00 in EtOAc, $R_f$=0.71 in 1:1 MeOH-EtOAc, $R_f$=0.52 in acetone, and $R_f$ 0.40 in 3:2 $CHCl_3$-MeOH. An ultraviolet spectrum of fusacandin A acquired in MeOH/0.01M NaOH contained a band at $\delta_{max}$=254 nm (ε=35,000) and end absorption. An infrared spectrum of fusacandin A acquired in microscope mode contained bands at 3372, 2955, 2927, 2858, 1702, 1634, 1459, 1411, 1375, 1335, 1396, 1267, 1146, 1076, 1049, and 1003 $cm^{-1}$.

Figure 4:
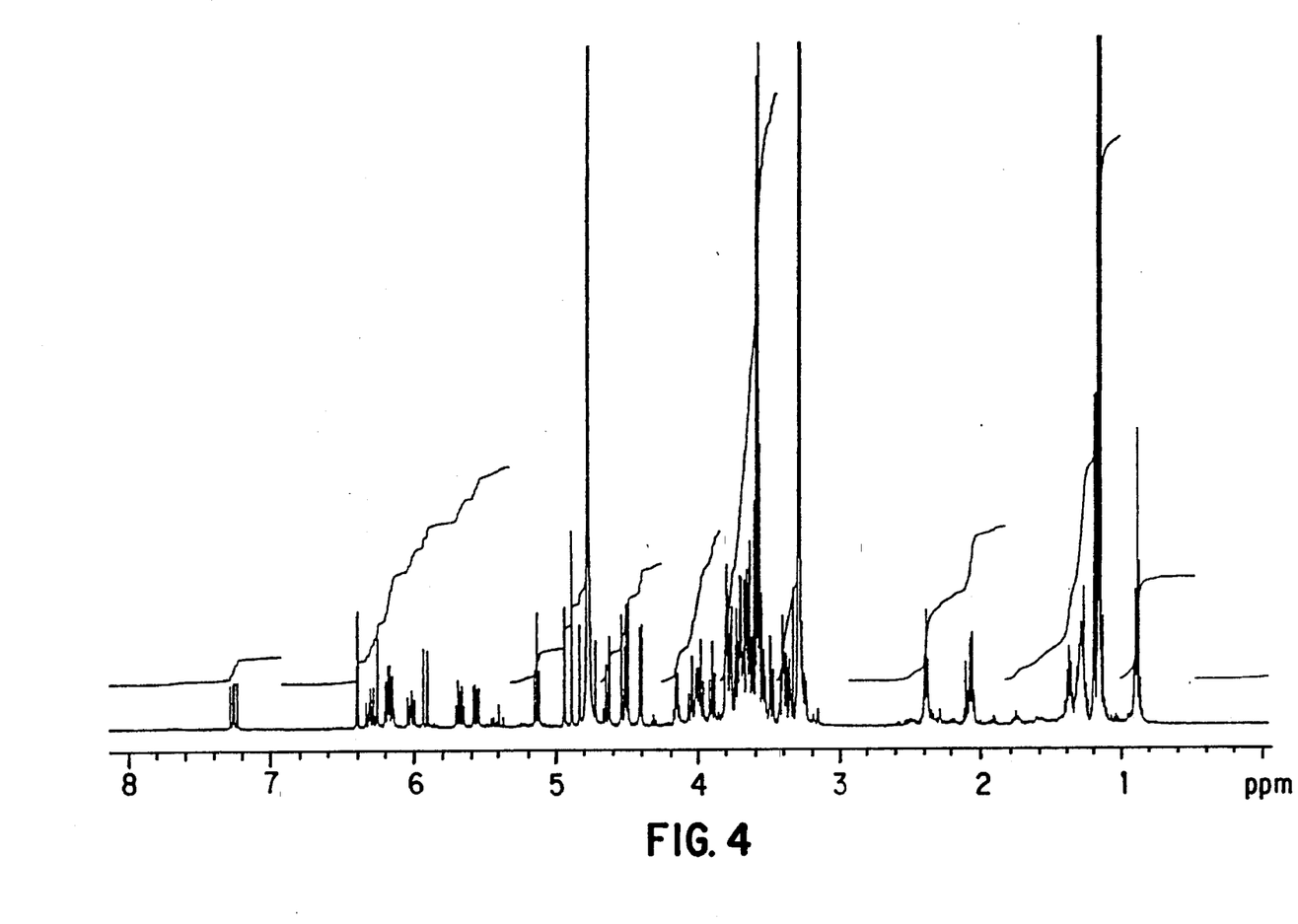
FIG. 4 is a proton NMR spectrum of Fusacandin B in $CD_3OD$.
Figure 5:
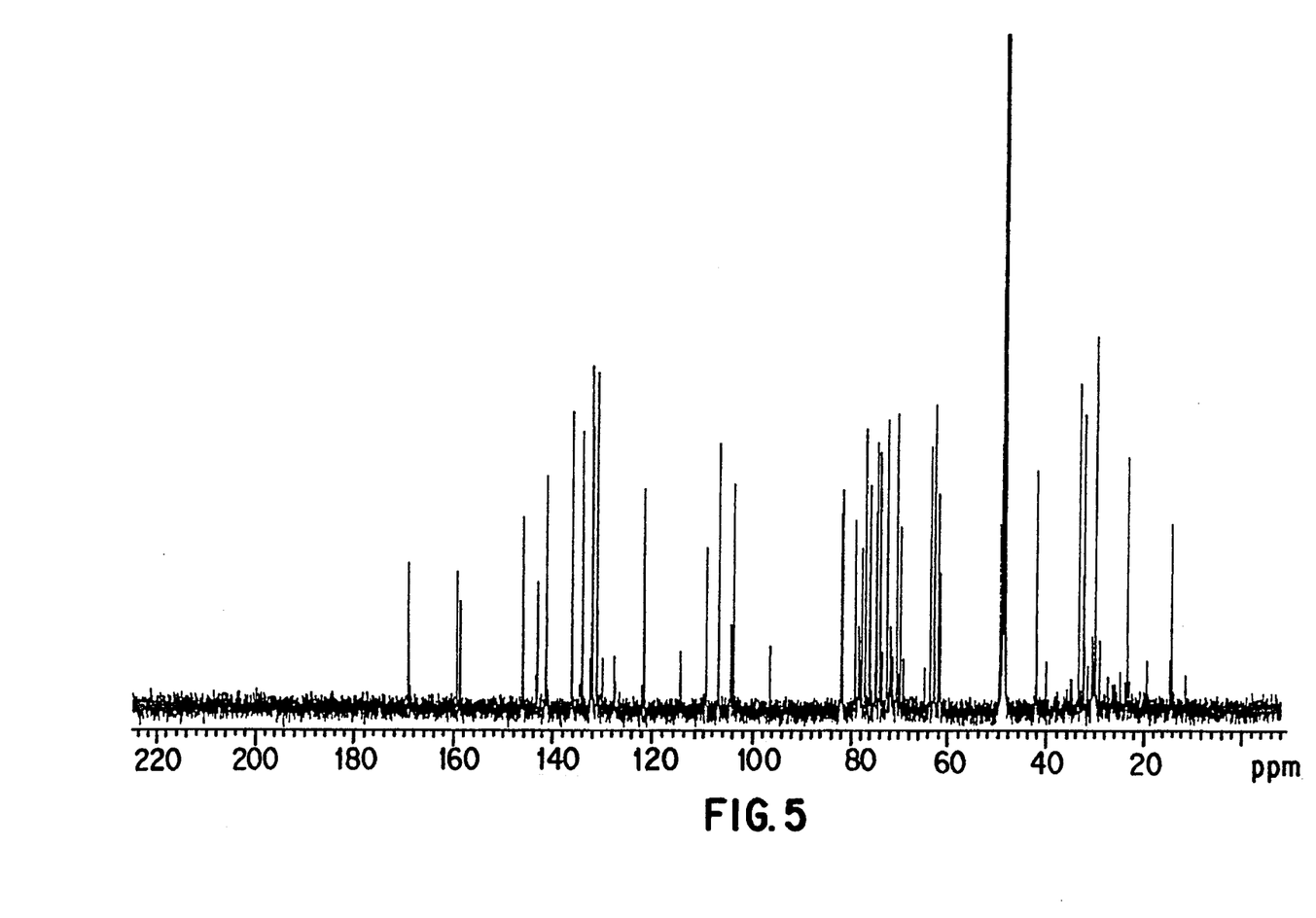
FIG. 5 is a carbon NMR spectrum of Fusacandin B in $CD_3OD$.
Figure 6:
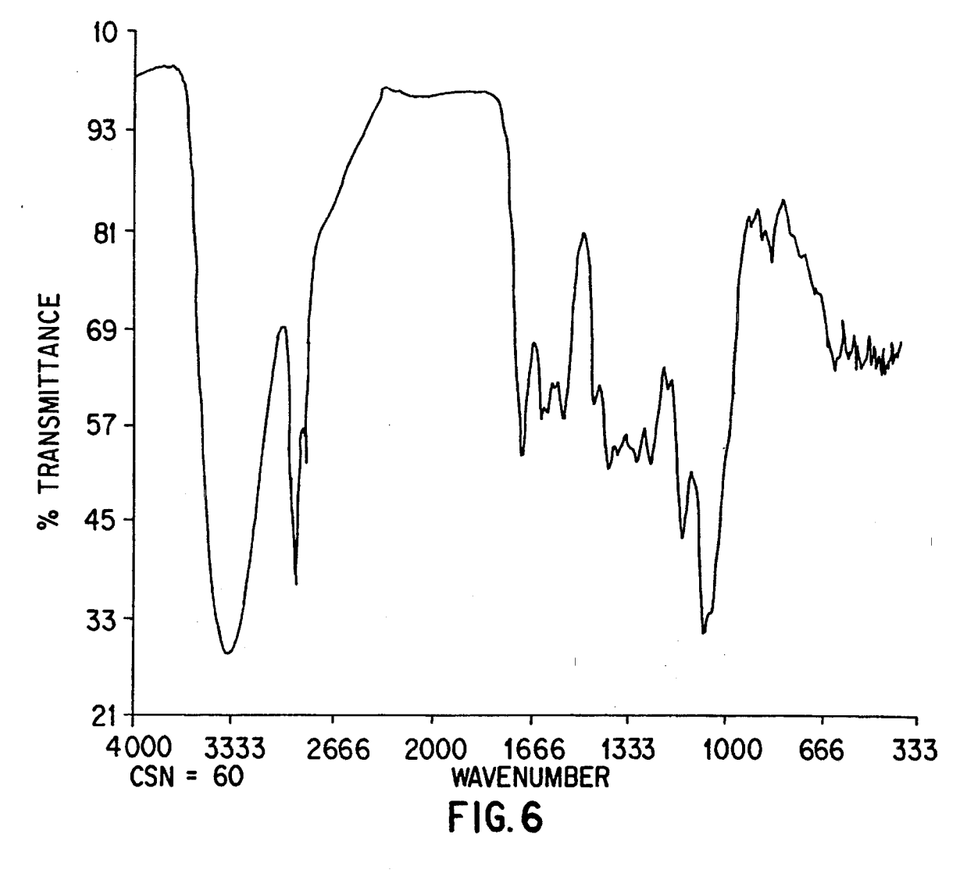
FIG. 6 is an IR spectrum of Fusacandin B acquired in microscope mode.

Fusacandin B was characterized using IR, UV, $^1H$ and $^{13}C$ NMR spectroscopy. The resulting infrared, proton and carbon spectra are shown in FIGS. 4, 5 and 6. Fusacandin B has a molecular weight of 872 ($C_{41}H_{60}O_{20}$) and is a white solid. m.p. 42–45° C. $[\alpha]_D=+1°$ (c=0.4, MeOH). TLC characterization on Merck silica gel plates: $R_f$=0.00 in EtOAc, $R_f$=0.60 in 1:1 MeOH/EtOAc, $R_f$=0.46 in acetone and $R_f$=0.19 in 3:2 $CHCl_3$/MeOH. An ultraviolet spectrum of fusacandin B acquired in MeOH or MeOH/0.01M HCl contained a band at $\delta_{max}$=263 nm (ε=18,000), 231 (21,000) and end absorption. An ultraviolet spectrum of fusacandin B acquired in MeOH/0.01M NaOH contained a band at $\delta_{max}$=256 nm (ε=22,000), and end absorption. An infrared spectrum of fusacandin B acquired in microscope mode contained bands at: 3305, 3040, 3005, 2880, 2850, 1708, 1645, 1625, 1570, 1465, 1410, 1380, 1315, 1265, 1155, 1080 and 1055 $cm^{-1}$.

EXAMPLE 8

In Vitro Assay of Antifungal Activity

Minimal inhibitory concentrations (MICs) were determined by an agar dilution method. The test compounds were serially diluted in MeOH and 0.2 mL portions were mixed with 20 mL of molten, cooled Sabouraud dextrose agar (Difco). Yeast cell inoculum was prepared by growing cultures on Sabouraud dextrose agar for 18 hours at 32° C. and suspending the cells in phosphate buffered saline. Filamentous fungi were grown under the same conditions for 4 days to obtain spores. The inoculum level for all cultures was adjusted to $10^4$ cells using a Petroff-Hauser cell counter. The glutarimide antifungal compounds cycloheximide or amphotericin B were used as a control. Inoculated test plates were incubated at 32° C. and examined after 20 hours. The results, shown in Tables 5a and 5b, demonstrate that the compounds of the present invention possess significant antifungal activity.

TABLE 5a

| In Vitro Antifungal Activity of Fusacandin A MIC (μg/ml) | | |
| --- | --- | --- |
| Microorganism | Fusacandin A | Cycloheximide |
| *Candida albicans* CCH 442 | 6.26 | >100 |
| *Candida albicans* ATCC997 | 12.5 | >100 |
| *Candida albicans* ATCC 623 | 6.25 | >100 |

TABLE 5a-continued

In Vitro Antifungal Activity of Fusacandin A
MIC (µg/ml)

| Microorganism | Fusacandin A | Cycloheximide |
|---|---|---|
| Candida tropicalis NRRL-Y-1 | 6.25 | 0.4 |
| Candida kefyr ATTC 288 | 6.25 | |
| Torulopsis glabrata ATCC 155 | 3.12 | 0.4 |
| Saccharomyces cereviseae GS 1-36 | 3.12 | <0.05 |
| Aspergillus niger ATCC 164 | 6.25 | 1.6 |
| Nocardia asteroides ATTC 9970 | 12.5 | 1.6 |
| Streptococcus pyrogenes EES61 | 6.25 | 50 |
| Streptococcus bovis A-5169 | 12.5 | 25 |
| Staphylococcus aureus ATTC 6538p | 50 | 0.8 |

TABLE 5b

In Vitro Antifungal Activity of Fusacandin B
MIC (µg/ml)

| Microorganism | Fusacandin B | Amphotericin B |
|---|---|---|
| Cryptococcus albidus ATCC 341 | >100 | 3.12 |
| Saccharomyces cereviseae GS 1-36 | 50 | 1.56 |
| Aspergillus niger ATCC 164 | >100 | 1.56 |
| Candida albicans ATCC 102 | 50 | 1.56 |
| Candida albicans 579a | 50 | 1.56 |
| Candida albicans CCH 442 | 50 | 1.56 |
| Candida albicans ATCC 382 | >100 | 50 |
| Candida albicans ATCC 623 | 100 | 1.56 |
| Candida tropicalis NRRL Y-1 | 50 | 1.56 |
| Candida kefyr ATCC 288 | 100 | 1.56 |
| Torulopsis glabrata ATCC 155 | 100 | 1.56 |

EXAMPLE 9

In Vitro Inhibition of (1,3)-β-Glucan Synthase Activity

The fungal cell wall serves as a protective barrier and is essential for viability in a hypotonic environment. (1,3)-β-Glucan is a component of the Candida albicans cell wall, and the enzyme that biosynthesizes this polymer, glucan synthase, is not present in higher eukaryotes. (Glucan synthase is an integral plasma membrane protein that catalyzes polymerization of uridine diphosphate-glucose (UDP-Glc) into β-glucan.) Accordingly, glucan synthase represents an ideal target for the development of antifungal agents.

A microtiter screen was established to detect inhibitors of (1,3)-β-glucan formation in C. albicans cell free extracts. Microsomes isolated from mid-log phase grown yeast were incubated with [$^{14}$C]UDP-Glc, effectors and test compound (fusacandin A). The formation of the water-insoluble β-glucan product was measured on a filter after removing the substrate with water washes. The IC$_{50}$ for fusacandin A was shown to be 20.5 µg/mL compared to 3.6 µg/mL for papulacandin B. The minimum inhibitory concentration (MIC) for fusacandin was 0.5 µg/mL compared to 1.0 µg/mL for papulacandin B.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art, and may be made without departing from the spirit and scope thereof.

What is claimed is:

1. A compound having the formula wherein R is selected from the group consisting of hydrogen and a radical having the formula or a pharmaceutically acceptable prodrug thereof.

2. A compound according to claim 1 wherein R is hydrogen.

3. A compound according to claim 1 wherein R is a radical having the formula

4. A pharmaceutical composition comprising a compound according to claim 1 in combination with a pharmaceutically acceptable carrier.

5. A pharmaceutical composition comprising a compound according to claim 2 in combination with a pharmaceutically acceptable carrier.

6. A pharmaceutical composition comprising a compound according to claim 3 in combination with a pharmaceutically acceptable carrier.

7. A method of treating a fungal infection in a patient in need of such treatment, comprising administering to the patient a therapeutically effective amount of a compound according to claim 1.

8. A method of treating a fungal infection in a patient in need of such treatment, comprising administering to the patient a therapeutically effective amount of a compound according to claim 2.

9. A method of treating a fungal infection in a patient in need of such treatment, comprising administering to the patient a therapeutically effective amount of a compound according to claim 3.

10. A process for preparing a compound according to claim 1, comprising the steps of (a) culturing a microorganism having the characteristics of Fusarium species AB 1900A-1314 under suitable conditions in a fermentation medium containing assimilable sources of carbon and nitrogen;

(b) allowing the compound to accumulate in the fermentation medium; and (c) isolating the compound from the fermentation medium.

11. A process according to claim 10 wherein the microorganism is Fusarium strain NRRL 21252.

* * * * *